(12) United States Patent
Hassad

(10) Patent No.: US 11,547,630 B1
(45) Date of Patent: Jan. 10, 2023

(54) INTRAVENOUS "Y" SHAPED (YASEEN) ADAPTER

(71) Applicant: Omar Hassad, New Lenox, IL (US)

(72) Inventor: Omar Hassad, New Lenox, IL (US)

(*) Notice: Subject to any disclaimer, the term of this patent is extended or adjusted under 35 U.S.C. 154(b) by 0 days.

(21) Appl. No.: 17/870,549

(22) Filed: Jul. 21, 2022

(51) Int. Cl.
*A61J 1/14* (2006.01)
*A61M 5/00* (2006.01)
*A61K 9/00* (2006.01)

(52) U.S. Cl.
CPC .............. *A61J 1/1481* (2015.05); *A61M 5/00* (2013.01); *A61M 5/002* (2013.01); *A61K 9/00* (2013.01)

(58) Field of Classification Search
CPC ...... A61J 1/2013; A61J 1/2089; A61J 1/2058; A61M 39/10; A61M 39/105; A61M 39/1055; A61M 2039/1077; A61M 2039/1083; A61M 2039/1088; A61M 39/146
See application file for complete search history.

(56) References Cited

U.S. PATENT DOCUMENTS

| | | | |
|---|---|---|---|
| 5,893,397 A * | 4/1999 | Peterson | A61J 1/2096 141/378 |
| 9,669,206 B2 | 6/2017 | Spohn | |
| 9,925,329 B2 | 3/2018 | Reichert | |
| 2004/0064097 A1 | 4/2004 | Peterson | |
| 2006/0089604 A1* | 4/2006 | Guerrero | A61M 5/1408 604/247 |
| 2022/0151875 A1* | 5/2022 | Kim | A61J 1/2058 |

* cited by examiner

*Primary Examiner* — Bradley J Osinski

(57) ABSTRACT

An IV adapter to allow for the mixing of multiple compatible medications with one another using a single bag of intravenous fluid. The IV adapter has multiple arms extending which gives rise to the ability to mix multiple medications. There is a spike within each arm to puncture the medication. The plurality of arms have built in mechanisms to control the flow of the medication and stop it from flowing in a certain direction. There are connections at the end of each arm allowing for a tight seal to be made to prevent any medication from leaking out of the IV line.

16 Claims, 10 Drawing Sheets

US 11,547,630 B1

INTRAVENOUS "Y" SHAPED (YASEEN) ADAPTER

FIELD OF THE INVENTION

The present invention relates generally to a medical device. More specifically, the present invention is a device that aids in administering multiple medications at once through an intravenous line.

BACKGROUND OF THE INVENTION

Intravenous(IV) lines are a very important tool medical professionals use to administer medications to a patient in a hospital setting. Not all medication is capable of being administered orally or even if capable of being administered orally, not all patients are capable of swallowing. Additionally, if a patient has more than one bag of medication that needs to be hung, an intravenous(IV) fusion line is limited to one spike or needle only allowing a single bag of medication to be hung at once.

An objective of the present invention is to provide users with an IV adapter that allows for multiple medications to be mixed and administered at once using a single intravenous port. The present invention intends to provide users with a device that has multiple arms allowing for the attachment of more than one bag, allowing for medications to be mixed within the same intravenous bag. In order to accomplish that, a preferred embodiment of the present invention comprises a first arm, a second arm, a third arm, with two of the three arms having a snap cap adapted to be attached medication vials. Thus, the present invention is an adapter to allow compatible medication to be mixed and administered to a patient.

SUMMARY OF THE INVENTION

The present invention is an adapter to allow nurses, doctors, pharmacists, and other medical professional to mix compatible medication in a single intravenous port without the need to have secondary piggyback lines involved. The present invention seeks to provide users with a device that can attach at least one medication vile and mix the medication in a single IV bag of fluid. The adapter is designed to be connected to a bag of intravenous fluid on one end and at least one vial of medication on one of the other two arms. The IV bag with the adapter and vial of medication is turned upside down allowing the medication to flow in to the IV fluid bag. Once mixed, the block mechanism is engaged closing off ability for the IV fluid to flow back to the medication vial, leaving fluid to travel down the IV line and into a patient's body.

The adapter comprises a first arm, a second arm, and a third arm. The second and third arm each have a universal vial fastener allowing a medication vial to be connected to the adapter. Each universal vial fastener has a finger flange that when depressed, engages the vial spike to puncture the medication vial, allowing the mixture of the medication to occur.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

Figure 1:
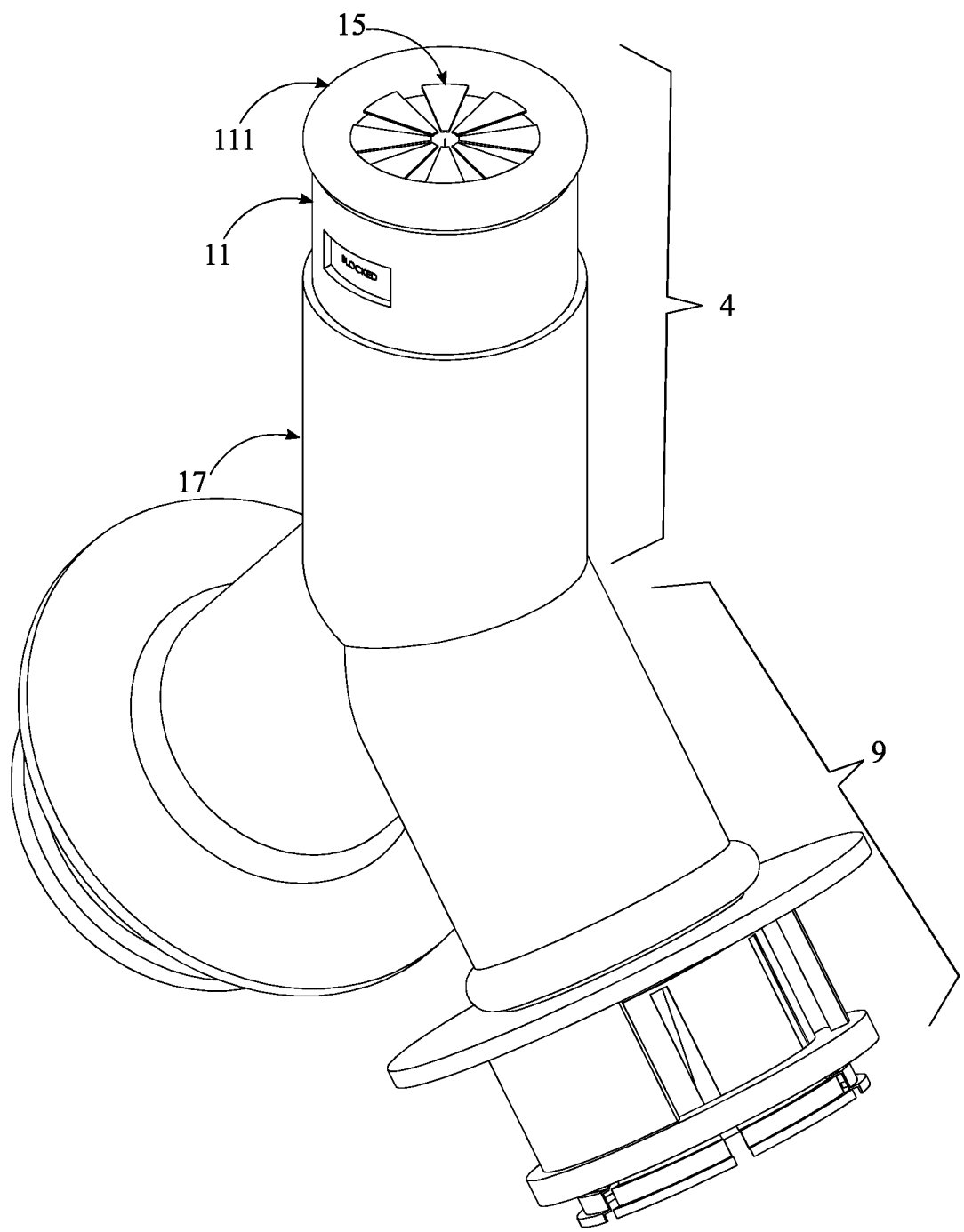
FIG. 1 is a top perspective view of the present invention.
Figure 2:
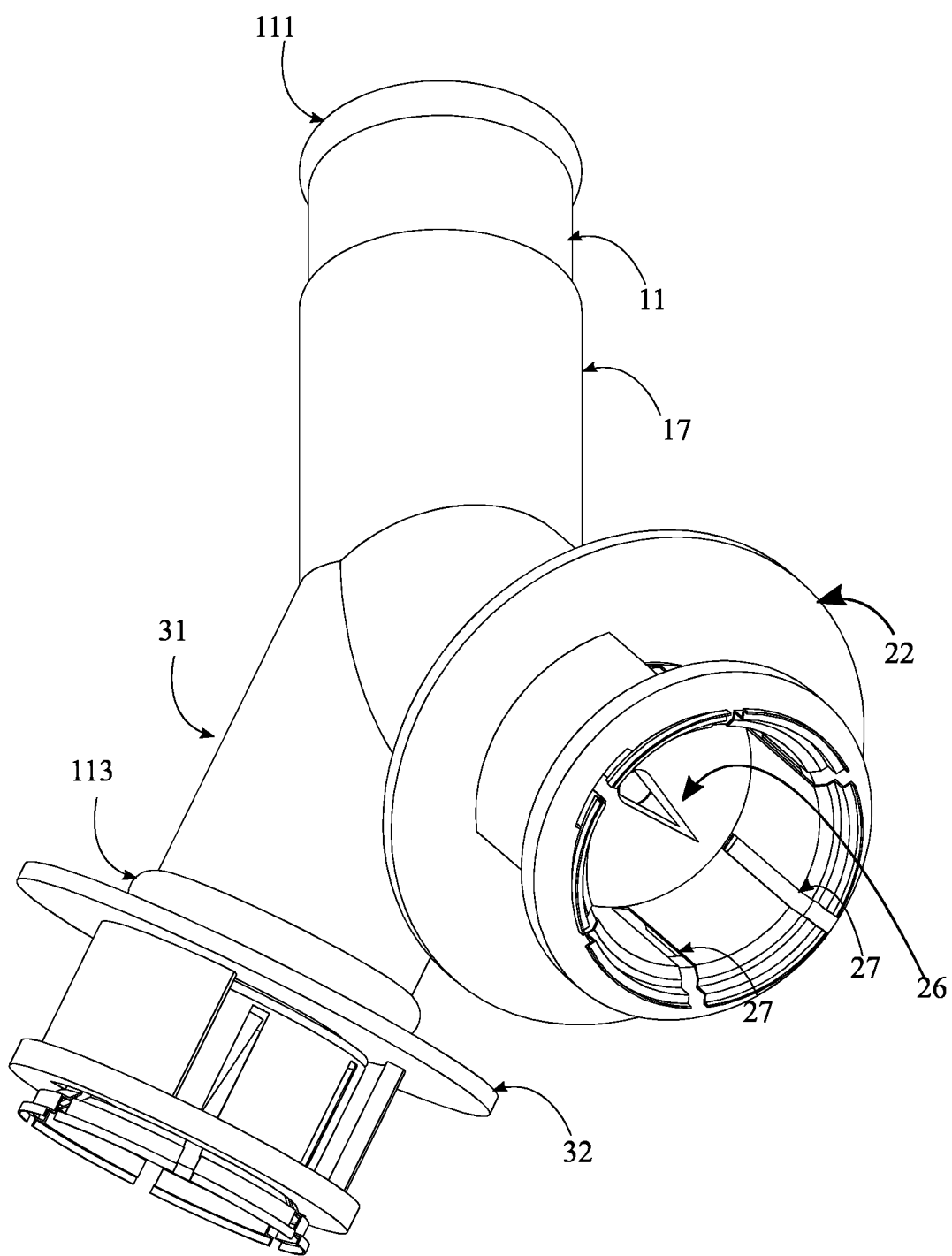
FIG. 2 is a bottom perspective view of the present invention.
Figure 3:
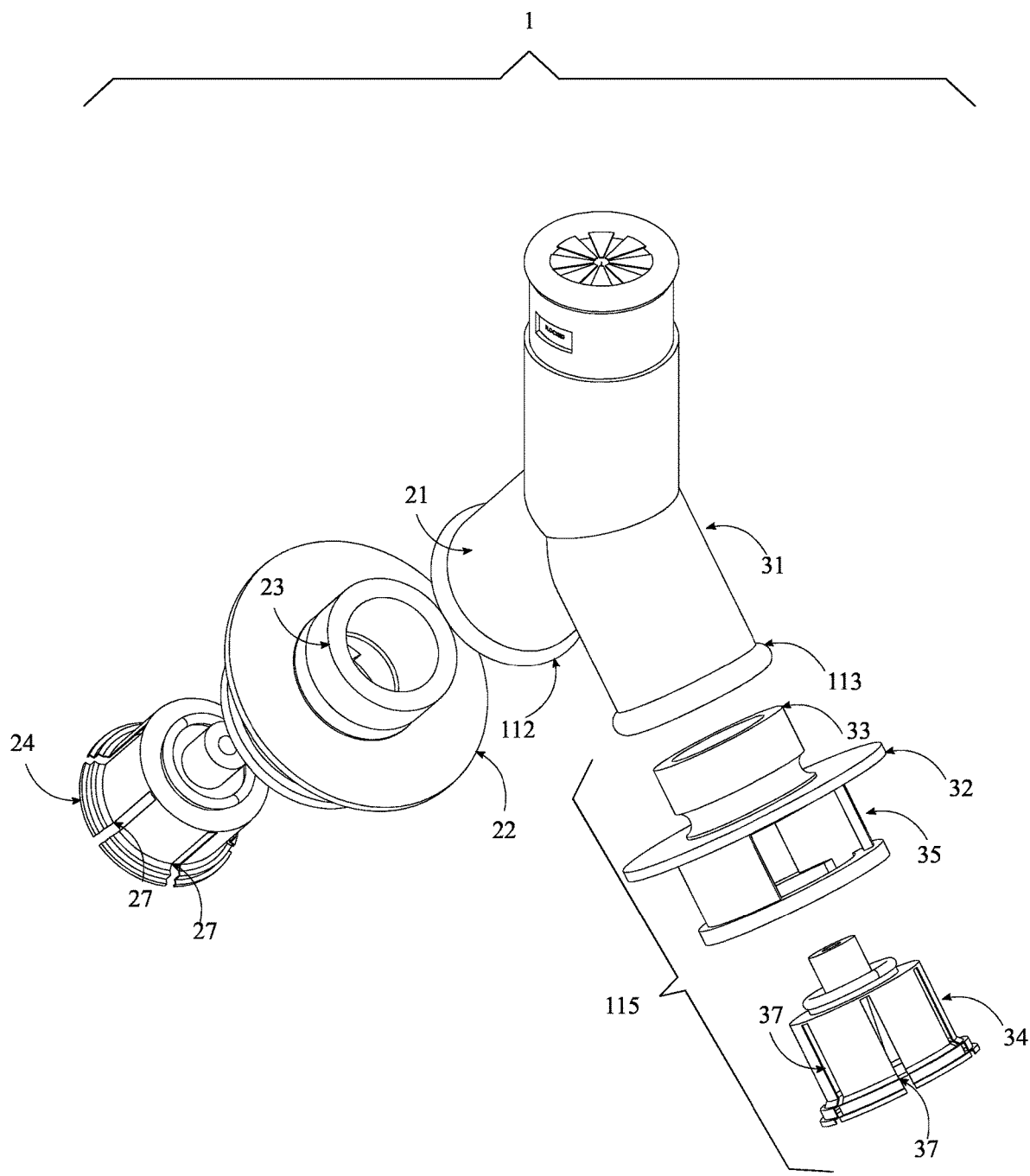
FIG. 3 is a right perspective exploded view of the present invention.
Figure 4:
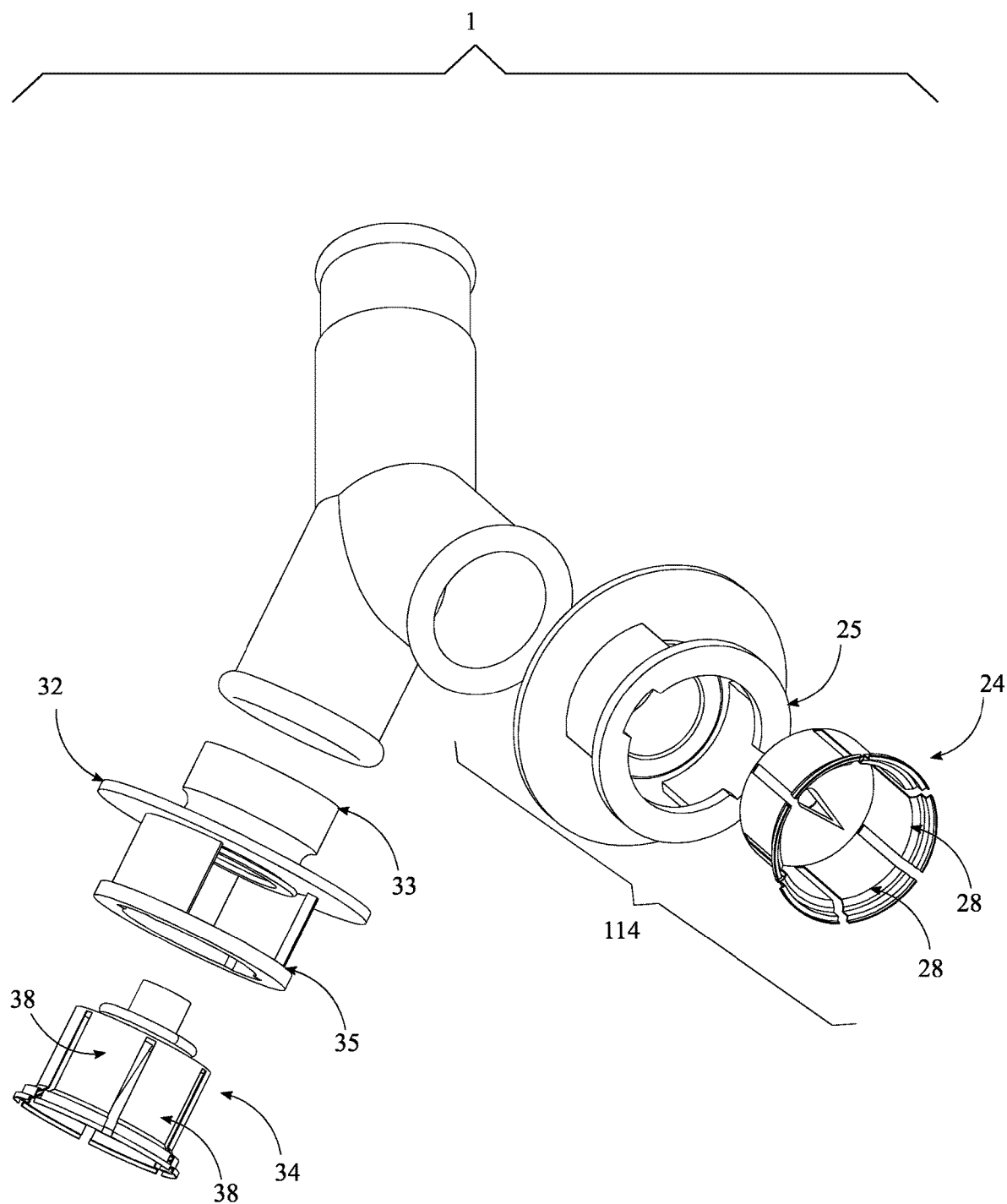
FIG. 4 is a left perspective exploded view of the present invention
Figure 5:
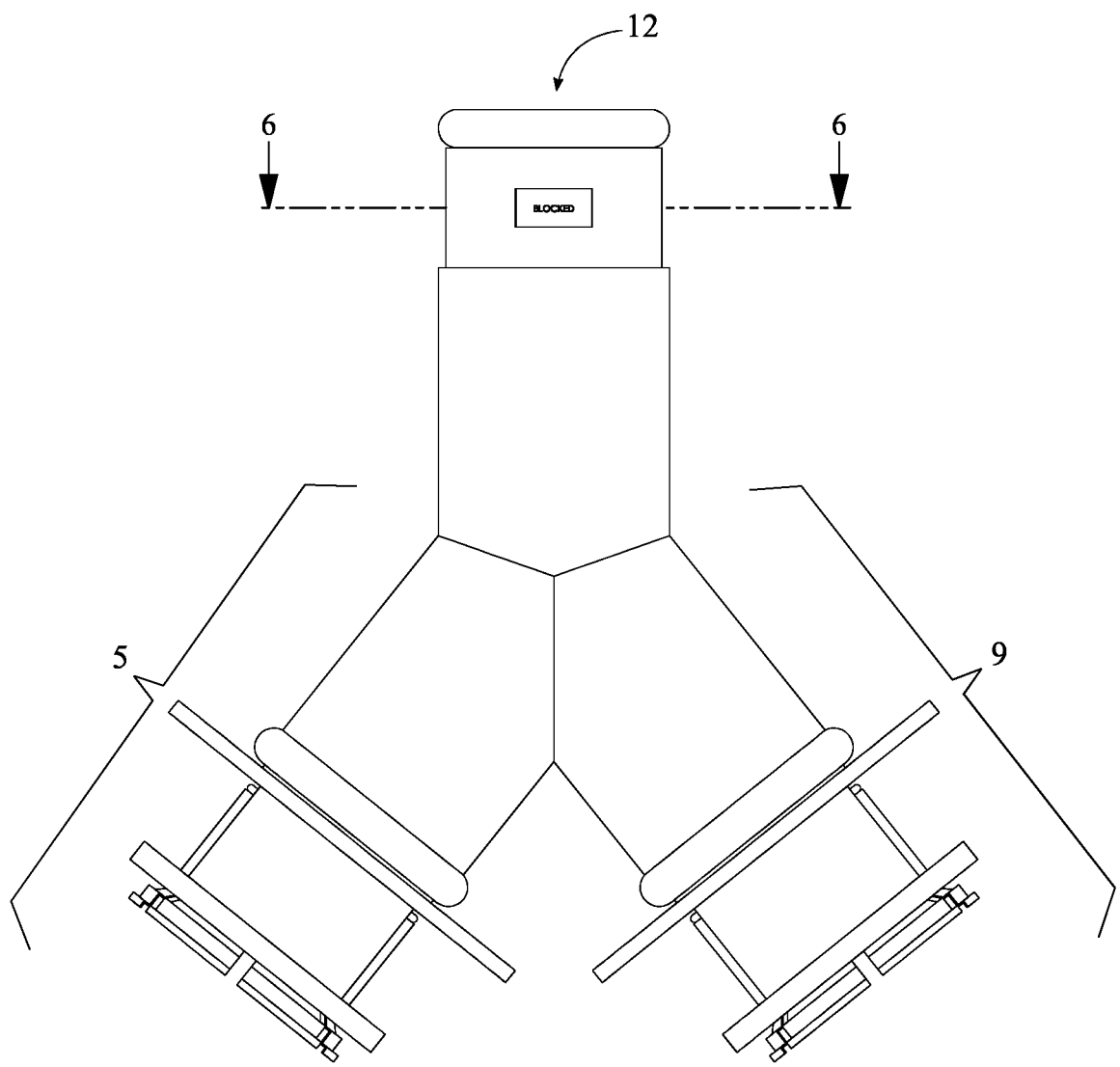
FIG. 5 is a front view of the present invention.
Figure 6:
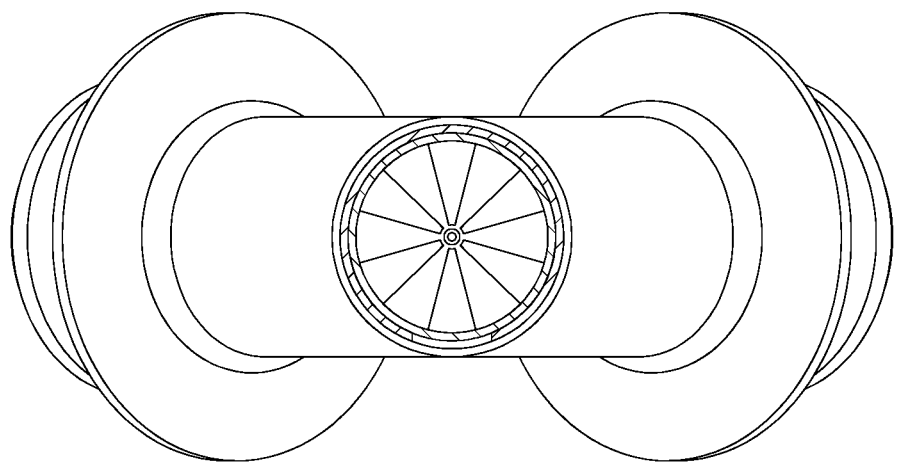
FIG. 6 is a top view of the present invention.
Figure 7:
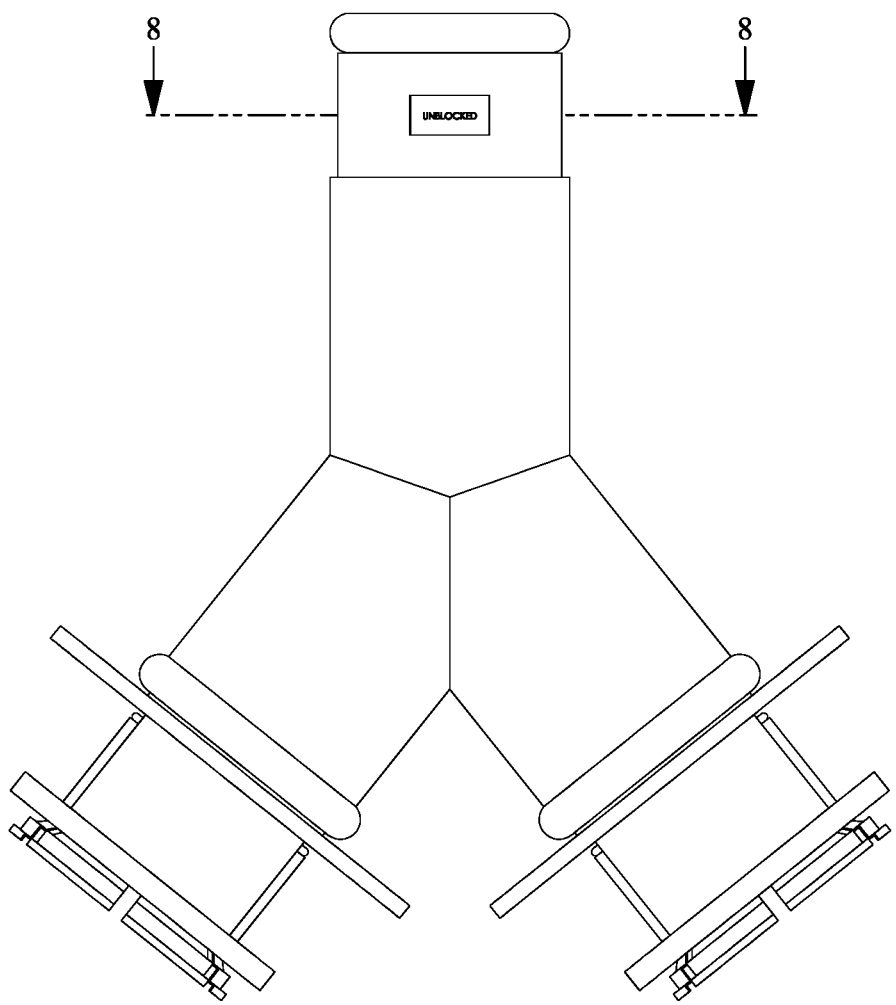
FIG. 7 is a front view of the present invention.
Figure 8:
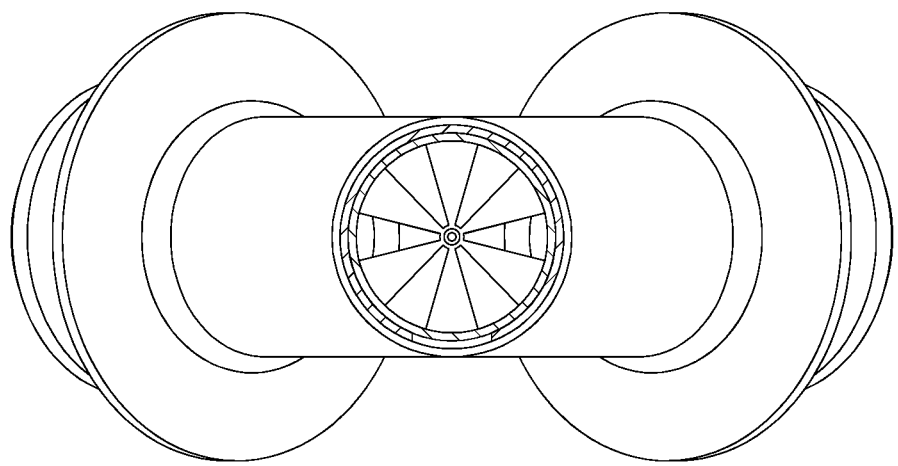
FIG. 8 is a cross-section view taken along line 8-8 in FIG. 7.
Figure 9:
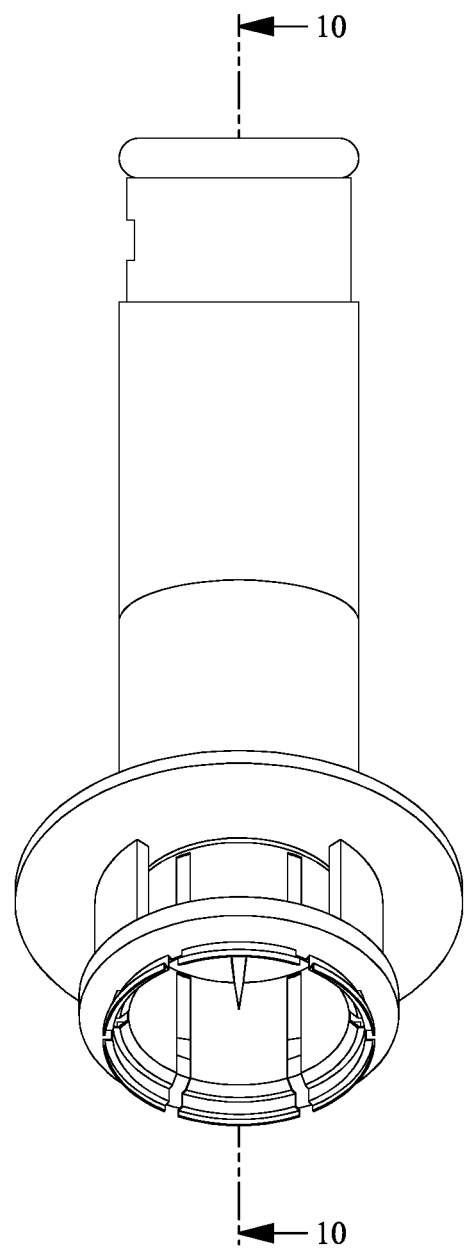
FIG. 9 is a side view of the present invention.

As shown in FIG. 1, the present invention is an adapter for use in intravenous lines and the administering of medication. An objective of the present invention is to provide medical professionals the ability to mix multiple compatible medication vials at once through a single intravenous port. The intravenous(IV) adapter 1 comprises a first arm 4, a second arm 5, and a third arm 9 attached together, with the arms extending in outwardly direction from the attachment point forming a "Y" shaped IV adapter 1 as shown in FIG. 5. These arms allow for a bag of intravenous fluid and a vial of medication to freely flow throughout an intravenous line and be mixed and administered to a patient through the same intravenous line. The first arm 4, second arm 5, and third arm 9 each have a female IV port connection, one respectively for each arm, perimetrically positioned on the distal end of each arm. The female IV port connection forms a seal around the connection of each arm to the component it is being attached to. The first arm 4, second arm 5, and third arm 9 are each a hollow cylindrical tube.

Figure 10:
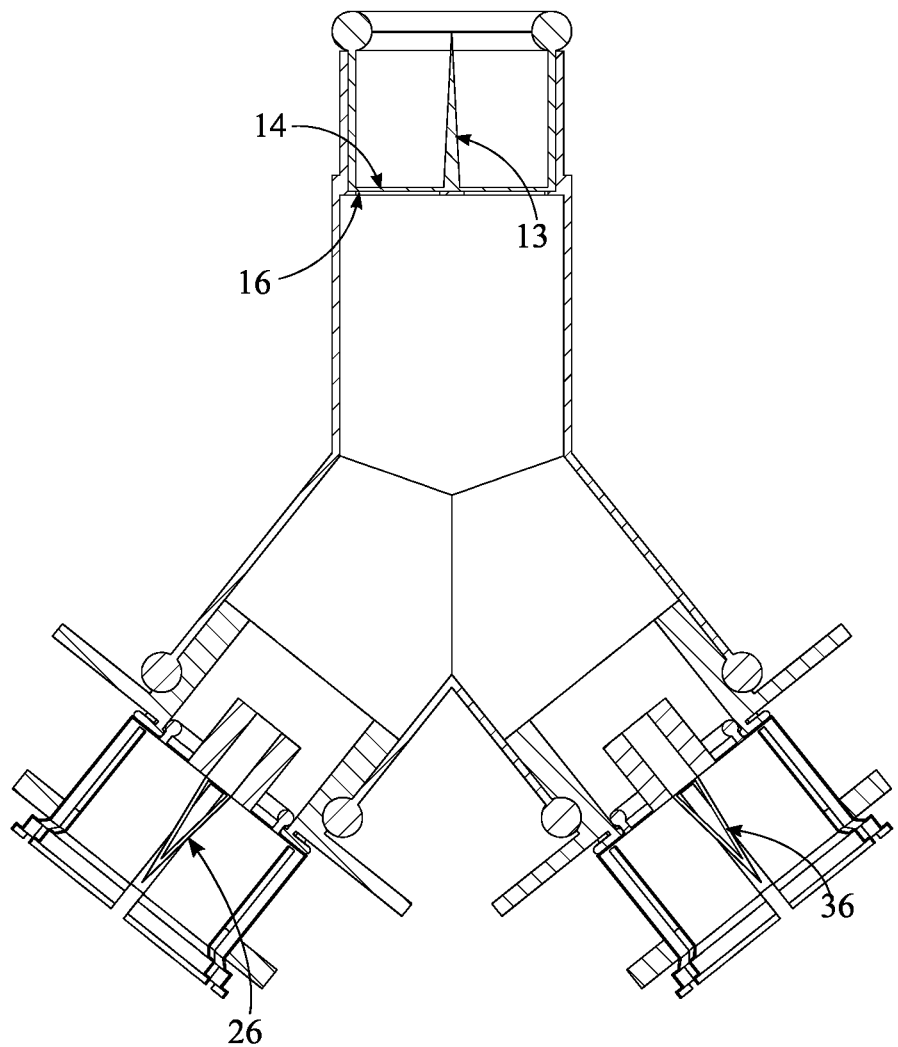
FIG. 10 is a cross-sectional view taken along line 10-10 in FIG. 9.

In its preferred embodiment, the IV adapter 1 is made out of plastic or any suitable material that maintains the integrity of the invention. The first arm 4 is hollow and comprises an outer arm body 17, an internal twisting shaft 11, an IV canal 12, an IV canal spike 13, a spike shelf 14, a plurality of IV canal flaps 15, and a block mechanism 16. The internal twisting shaft 11 is rotatably connected inside the outer arm body 17 of the first arm 4. Perimetrically attached at the distal end of the internal twisting shaft 11 is the female IV port connection of the first arm 111. The IV canal 12 is hollow pathway located inside of the first arm 4 and traverses the length of the first arm 4. Attached to the inside wall of the internal twisting shaft 11, a plurality of IV canal flaps 15 are fixedly attached. Located internally in the first arm 4, where the internal twisting shaft 11 connects with the outer arm body 17, a spike shelf 14 is diametrically positioned to support to the IV canal spike 13, which is fixedly attached to rest on the spike shelf 14 as shown in FIG. 10.

Located immediately below the spike shelf 14, a block mechanism 16 is diametrically positioned. The block mechanism 16 functions when the shaft of the internal twisting shaft 11 is spun in a certain direction, it engages the block mechanism 16 to open, allowing the flow of the medication through the IV port. When the internal twisting shaft 11 is twisted in the opposition direction, the block mechanism 16 prevents the flow of the medication.

The second arm 5 is a cylindrical hollow tube and comprises an arm body 21 and a first universal vial fastener 114. The second arm 5 has a distal end where a female IV port connection 112 is perimetrically around the second arm body 21 and positioned on the second arm body 21 so it is in direct contact with the first universal vial fastener 114. The second arm 5 is angularly offset from the first arm 4 and third arm 9. The first universal vial fastener 114 is comprised of a first finger flange 22, a first flow control mechanism 23, a first snap cap adapter 24, and a first twisting lock mechanism 25. The first snap cap adapter 24 is configured to connect with any vial of medication needing to be mixed with a bag of intravenous fluid. The first snap cap adapter 24 is a circular cap that comprises a plurality of first snap cap adapter plates 28 forming a circle and a plurality of first snap cap cavities 27 between the first snap cap adapter plates 28 allowing it to be snapped into place when mounted within the first twisting lock mechanism 25.

The plurality of first snap cap adapter plates 28 surrounds a first vial spike 26, with the first vial spike 26 being centrally positioned in the circle of first snap cap adapter plates 28. The first flow control mechanism 23 is at the top of the first universal vial fastener 114 that when connected to the second arm body 21 is positioned inside the second arm body 21 and is in direct contact with the female IV port connection of the second arm 112 as shown in FIG. 5. The first twisting lock mechanism 25 is positioned between the first snap cap adapter 24 and the first flow control mechanism 23. Connected to the first flow control mechanism 23 is the first twisting lock mechanism 25, which is twisted before the first vial spike 26 punctures a medication vial, locking the first universal vial fastener 114 in place on the medication vial. Positioned between the first flow control mechanism 23 and the first twisting lock mechanism 25 is the first finger flange 22. The first finger flange 22 is perimetrically positioned around the first flow control mechanism 23.

The first finger flange 22 is pressed downward which engages the first vial spike 26 to puncture the soft top of any medication vial thereby attaching the first universal vial fastener 114 to a medication vial. The first flow control mechanism 23 is a hollow cylindrical canal that is connected to the first twisting lock mechanism 25. The first twisting lock mechanism 25 is mounted on to the first snap cap adapter 24.

The third arm 9 is angularly offset from the first arm 4 and second arm 5. The third arm 9 is a cylindrical hollow tube and comprises an arm body 31 and a second universal vial fastener 115. The third arm 9 has a female IV port connection 113 perimetrically around the third arm body 31 so it is in direct contact with the second universal vial fastener 115. The third arm is angularly offset from the first arm 4 and the second arm 5. The second universal vial fastener 115 is comprised of a second finger flange 32, a second flow control mechanism 33, a second snap cap adapter 34, and a second twisting lock mechanism 35. The second snap cap adapter 34 is a circular cap that comprises a plurality of second snap cap adapter plates 38 forming a circle and a plurality of second snap cap cavities 37 between the second snap cap adapter plates 38 allowing it to be snapped into place when mounted within the second twisting lock mechanism 35.

The plurality of second snap cap adapter plates 38 surrounds a second vial spike 36, with the second vial spike 36 being centrally positioned in the circle of second snap cap adapter plates 38. The second snap cap adapter 34 is configured to connect with any vial of medication needing to be mixed with a bag of intravenous fluid. The second flow control mechanism 33 is at the top of the second universal vial fastener 115 that when connected to the third arm body 31 is positioned inside of the third arm body 31 and is in direct contact with the female IV port connection of the third arm 113. Connected to the second flow control mechanism 33 is the second twisting lock mechanism 35, which is twisted before the second vial spike 36 punctures a medication vial, locking the second universal vial fastener 115 in place on the medication vial. Positioned between the second flow control mechanism 33 and the second twisting lock mechanism 35 is the second finger flange 32. The second finger flange 32 is perimetrically positioned around the second flow control mechanism 33. The second twisting lock mechanism 35 is positioned between the second snap cap adapter 34 and the second flow control mechanism 33.

The second finger flange 32 is pressed downward which engages the second vial spike 36 to puncture the soft top of any medication vial thereby attaching the second universal vial fastener to a medication vial. The second flow control mechanism 33 is a hollow cylindrical canal that is connected to the second twisting lock mechanism 35. The second twisting lock mechanism 35 is configured to be mounted on to the second snap cap adapter.

Although the invention has been explained in relation to its preferred embodiment, it is to be understood that many other possible modifications and variations can be made without departing from the spirit and scope of the invention.

What is claimed is:
1. An intravenous(IV) adapter comprising:
a first arm;
a second arm;
a third arm;
the first arm, second arm, and third arm are attached together;
the first arm comprising an outer arm body and an internal twisting shaft;
the internal twisting shaft being rotably connected inside the outer arm body;
the second arm comprising an arm body and a first universal vial fastener; and
the third arm comprising an arm body and a second universal vial fastener;
a hollow IV canal which traverses the inside length of the first arm;
the internal twisting shaft having a plurality of IV canal flaps;
the plurality of IV canal flaps fixedly attached to the internal twisting shafts inner wall;
the first arm, second arm, and third arm each being a hollow cylindrical tube;
a spike shelf diametrically positioned internally in the first arm where the twisting shaft connects to the outer arm body; and
an IV canal spike fixedly attached to rest on the spike shelf.

2. The IV adapter as in claim 1 further comprising:
the first arm having an attached end and a distal end;
a female IV port connection perimetrically positioned on the distal end of the first arm;
the first arm being angularly offset from the second arm and third arm;
the second arm being angularly offset from the first and third arm; and
a block mechanism being diametrically positioned underneath the spike shelf.

3. The IV adapter as in claim 2 further comprising:
a female IV port connection perimetrically positioned on the distal end of the second arm around a second arm body; and
the first universal vial fastener comprising a first finger flange and a first flow control mechanism.

4. The IV adapter as in claim 3 further comprising:
the first universal vial fastener further comprising a first snap cap adapter and a first twisting lock mechanism;
the first snap cap adapter having a first vial spike; and
the first twisting lock mechanism is configured to be mounted on to the first snap cap adapter.

5. The IV adapter of claim 4 further comprising:
first twisting lock mechanism is positioned between the first snap cap adapter and the first flow control mechanism; and
the first snap cap adapter having a plurality of first snap cap cavities between the plurality of first snap cap plates of the first snap cap adapter.

6. The IV adapter as in claim 3 further comprising:
the first snap cap adapter comprising a plurality of first snap cap adapter plates forming a circle; and
the first vial spike being centrally positioned in the circle of first snap cap plates.

7. The IV adapter as in claim 3 further comprising:
the first universal vial fastener having a top end;
the first flow control mechanism being at the top of the first universal vial fastener in direct contact with the female IV port connection of the second arm; and
the first finger flange perimetrically positioned around the first flow control mechanism.

8. The IV adapter as in claim 1 further comprising:
the third arm having an attached end and a distal end;
a female IV port connection perimetrically positioned on the distal end of the third arm around a third arm body;
the second universal vial fastener comprising a second finger flange and a second flow control mechanism;
the second universal vial fastener having a top and a bottom;
the second flow control mechanism being at the top of the second universal vial fastener in direct contact with the female IV port connection of the third arm; and
the second finger flange perimetrically positioned around the second flow control mechanism.

9. The IV adapter of claim 8 further comprising:
the second universal vial fastener further comprising a second snap cap adapter and a second twisting lock mechanism;
the second twisting lock mechanism is mounted on to the second snap cap adapter; and
the second twisting lock mechanism is positioned between the second snap cap adapter and the second flow control mechanism.

10. The IV adapter of claim 9 further comprising:
the second snap cap adapter comprising a plurality of second snap cap adapter plates forming a circle;
a second vial spike being centrally positioned in the circle of second snap cap plates; and
the second snap cap adapter having a plurality of second snap cap cavities between the plurality of second snap cap plates.

11. An intravenous(IV) adapter comprising:
a first arm;
a second arm;
a third arm;
the first arm, second arm, and third are attached together;
the first arm comprising an outer arm body and an internal twisting shaft;
the internal twisting shaft being rotably connected inside the outer arm body;
the second arm comprising an arm body and a first universal vial fastener;
the third arm comprising an arm body and a second universal vial fastener;
a hollow IV canal which traverses the inside length of the firm arm;
the internal twisting shaft having a plurality of IV canal flaps;
the plurality of IV canal flaps fixedly attached to the internal twisting shafts inner wall;
the first arm, second arm, and third arm each being a hollow cylindrical tube; and
the first universal vial fastener comprising a first finger flange and a first flow control mechanisms;
the first arm and second arm each having an attached end and a distal end;
a female IV port connection perimetrically positioned on the distal end of the first arm;
the second arm having a female IV port connection at the distal end of the second arm around a second arm body;
a spike shelf diametrically positioned internally in the first arm where the twisting shaft connects to the outer arm body; and
a block mechanism being diametrically positioned underneath the spike shelf.

12. The IV adapter as in claim 11 further comprising:
an IV canal spike fixedly attached to rest on the spike shelf;
the first arm being angularly offset from the second arm and third arm;
the second arm being angularly offset from the first and third arm;
the first universal vial fastener comprising a first snap cap adapter and a first twisting lock mechanism;
the first snap cap adapter having a first vial spike;
the first snap cap adapter comprising a plurality of first snap cap adapter plates forming a circle;
the first vial spike being centrally positioned in the circle of first snap cap plates; and
the first twisting lock mechanism is mounted on to the first snap cap adapter.

13. The IV adapter as in claim 12 further comprising:
the first universal vial fastener having a top end;
the first flow control mechanism being at the top of the first universal vial fastener in direct contact with the female IV port connection of the second arm;
the first finger flange perimetrically positioned around the first flow control mechanism;
the first twisting lock mechanism is positioned between the first snap cap adapter and the first flow control mechanism; and the first snap cap adapter having a plurality of first snap cap cavities between the plurality of first snap cap plates of the first snap cap adapter.

14. The IV adapter as in claim 11 further comprising:

the third arm having an attached end and a distal end;

a female IV port connection perimetrically positioned on the distal end of the third arm around the third arm body;

a second universal vial fastener comprising a second finger flange and a second flow control mechanism;

the second flow control mechanism being at the top of the second universal vial fastener in direct contact with the female IV port connection of the third arm; and a second finger flange perimetrically positioned around the second flow control mechanism.

15. The IV adapter as in claim 14 further comprising:

the second universal vial fastener further comprising a second snap cap adapter and a second twisting lock mechanism; and the second twisting lock mechanism is mounted on to the second snap cap adapter.

16. The IV adapter as in claim 15 further comprising:

the second twisting lock mechanism is positioned between the second snap cap adapter and the second flow control mechanism;

the second snap cap adapter comprising a plurality of second snap cap adapter plates forming a circle;

the second snap cap adapter comprising a plurality of second snap cap adapter plates forming a circle;

a second vial spike being centrally positioned in the circle of second snap cap plates; and the second snap cap adapter having a plurality of second snap cap cavities between the plurality of second snap cap plates.

* * * * *